(12) United States Patent
Naor

(10) Patent No.: US 9,750,604 B2
(45) Date of Patent: *Sep. 5, 2017

(54) HEART VALVE PROSTHESIS WITH COLLAPSIBLE VALVE AND METHOD OF DELIVERY THEREOF

(71) Applicant: Mitrassist Medical Ltd., Caesarea (IL)

(72) Inventor: Gil Naor, Hofit (IL)

(73) Assignee: Mitrassist Medical Ltd., Caesarea (IL)

( * ) Notice: Subject to any disclaimer, the term of this patent is extended or adjusted under 35 U.S.C. 154(b) by 74 days.

This patent is subject to a terminal disclaimer.

(21) Appl. No.: 14/242,898

(22) Filed: Apr. 2, 2014

(65) Prior Publication Data
US 2014/0214160 A1   Jul. 31, 2014

Related U.S. Application Data

(63) Continuation of application No. 12/726,338, filed on Mar. 17, 2010, now Pat. No. 9,078,751.

(60) Provisional application No. 61/257,979, filed on Nov. 4, 2009, provisional application No. 61/227,193, filed on Jul. 21, 2009, provisional application No. 61/186,100, filed on Jun. 11, 2009, provisional application No. 61/215,944, filed on May 12, 2009, provisional application No. 61/212,459, filed on Apr. 13, 2009, provisional application No. 61/210,255, filed on Mar. 17, 2009.

(51) Int. Cl.
*A61F 2/24* (2006.01)

(52) U.S. Cl.
CPC .......... *A61F 2/2418* (2013.01); *A61F 2/2436* (2013.01); *A61F 2/2442* (2013.01); *A61F 2/2445* (2013.01); *A61F 2/2448* (2013.01); *A61F 2/2496* (2013.01); *A61F 2220/0008* (2013.01); *A61F 2220/0016* (2013.01)

(58) Field of Classification Search
CPC .... A61F 2/2418; A61F 2/2442; A61F 2/2445; A61F 2/2448; A61F 2220/0016
See application file for complete search history.

(56) References Cited

U.S. PATENT DOCUMENTS 4,106,129 A   8/1978   Carpentier et al.
6,478,819 B2  11/2002  Moe
(Continued)

FOREIGN PATENT DOCUMENTS

JP   2005-505343   2/2005
JP   2005-535384   11/2005
(Continued)

OTHER PUBLICATIONS

Official Action Dated Nov. 12, 2014 From the US Patent and Trademark Office Re. U.S. Appl. No. 12/726,338.
(Continued)

*Primary Examiner* — Brian Dukert

(57) ABSTRACT

A valve prosthesis is adapted to operate in conjunction with native heart valve leaflets. The prosthesis includes an annulus and a skirt extending from the annulus. The skirt may be configured to be positioned through a native heart valve annulus, and the skirt may be movable between an open configuration permitting blood flow through the skirt and a closed configuration blocking blood flow through the skirt in cooperation with opening and closing of the native heart valve leaflets.

17 Claims, 17 Drawing Sheets

(56) References Cited

U.S. PATENT DOCUMENTS

| | | | |
|---|---|---|---|
| 6,726,717 | B2 | 4/2004 | Alfieri et al. |
| 7,381,220 | B2 | 6/2008 | Macoviak et al. |
| 8,092,520 | B2 | 1/2012 | Quadri |
| 2001/0010017 | A1 | 7/2001 | Letac et al. |
| 2001/0049556 | A1 | 12/2001 | Moe |
| 2003/0199975 | A1 | 10/2003 | Gabbay |
| 2004/0127982 | A1* | 7/2004 | Machold ............... A61F 2/2418 623/2.36 |
| 2004/0243230 | A1* | 12/2004 | Navia ................... A61F 2/2445 623/2.36 |
| 2005/0010287 | A1* | 1/2005 | Macoviak ............. A61F 2/2445 623/2.36 |
| 2005/0228495 | A1 | 10/2005 | Macoviak |
| 2006/0058871 | A1 | 3/2006 | Zakay et al. |
| 2006/0195183 | A1 | 8/2006 | Navia et al. |
| 2007/0010877 | A1 | 1/2007 | Salahieh et al. |
| 2007/0067029 | A1 | 3/2007 | Gabbay |
| 2007/0156233 | A1 | 7/2007 | Kapadia et al. |
| 2007/0185571 | A1 | 8/2007 | Kapadia et al. |
| 2007/0270943 | A1 | 11/2007 | Solem et al. |
| 2008/0065204 | A1 | 3/2008 | Macoviak et al. |
| 2008/0071362 | A1* | 3/2008 | Tuval ................... A61F 2/2418 623/2.1 |
| 2008/0208328 | A1 | 8/2008 | Antocci et al. |
| 2009/0005863 | A1 | 1/2009 | Goetz et al. |
| 2010/0280606 | A1 | 11/2010 | Naor |
| 2010/0298931 | A1 | 11/2010 | Quadri et al. |
| 2012/0078353 | A1 | 3/2012 | Quadri et al. |
| 2012/0215303 | A1 | 8/2012 | Quadri et al. |
| 2016/0038282 | A1 | 2/2016 | Naor |

FOREIGN PATENT DOCUMENTS

| | | |
|---|---|---|
| JP | 2007-536003 | 12/2007 |
| WO | WO 03/030776 | 4/2003 |
| WO | WO 2004/014258 | 2/2004 |
| WO | WO 2004/030568 | 4/2004 |
| WO | WO 2004/089250 | 10/2004 |
| WO | WO 2005/027797 | 3/2005 |
| WO | WO 2005/107650 | 11/2005 |
| WO | WO 2010/106438 | 9/2010 |

OTHER PUBLICATIONS

Applicant-Initiated Interview Summary Dated Jan. 20, 2015 From the US Patent and Trademark Office Re. U.S. Appl. No. 12/726,338.

Notice of Reason for Rejection Dated Sep. 26, 2014 From the Japanese Patent Office Re. Application No. 2012-5000334 and Its Translation Into English.

International Preliminary Report on Patentability Dated Sep. 29, 2011 From the International Bureau of WIPO Re. Application No. PCT/IB2010/000833.

International Search Report and the Written Opinion Dated Sep. 1, 2010 From the International Searching Authority Re. Application No. PCT/IB2010/000833.

Notice of Reason for Rejection Dated Jan. 24, 2014 From the Japanese Patent Office Re. Application No. 2012-5000334 and Its Translation Into English.

Official Action Dated Jul. 5, 2011 From the US Patent and Trademark Office Re. U.S. Appl. No. 12/726,338.

Official Action Dated Aug. 6, 2012 From the US Patent and Trademark Office Re. U.S. Appl. No. 12/726,338.

Official Action Dated Feb. 22, 2013 From the US Patent and Trademark Office Re. U.S. Appl. No. 12/726,338.

Official Action Dated Mar. 25, 2014 From the US Patent and Trademark Office Re. U.S. Appl. No. 12/726,338.

Official Action Dated Sep. 28, 2011 From the US Patent and Trademark Office Re. U.S. Appl. No. 12/726,338.

Official Action Dated Mar. 29, 2012 From the US Patent and Trademark Office Re. U.S. Appl. No. 12/726,338.

Restriction Official Action Dated Dec. 19, 2013 From the US Patent and Trademark Office Re. U.S. Appl. No. 12/726,338.

Restriction Official Action Dated Jul. 12, 2016 From the US Patent and Trademark Office Re. U.S. Appl. No. 14/797,218.

* cited by examiner

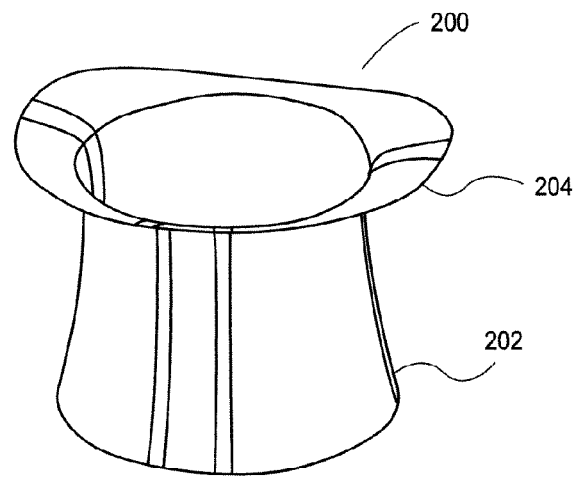
FIG. 2A
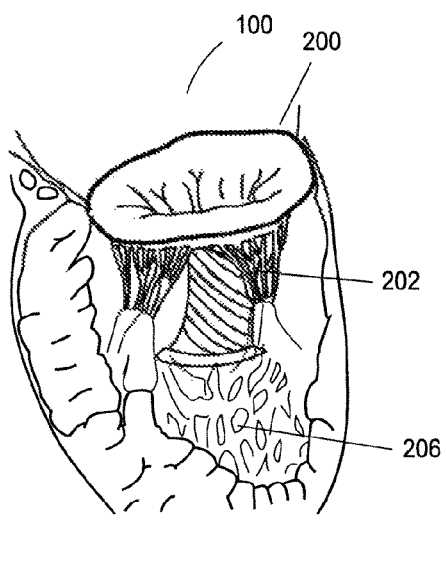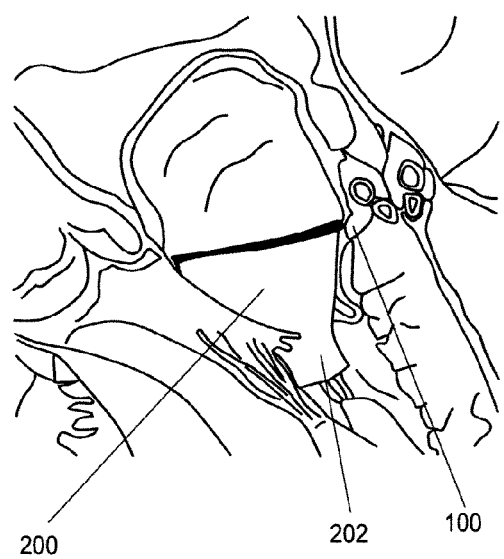
FIG. 2B  FIG. 2C

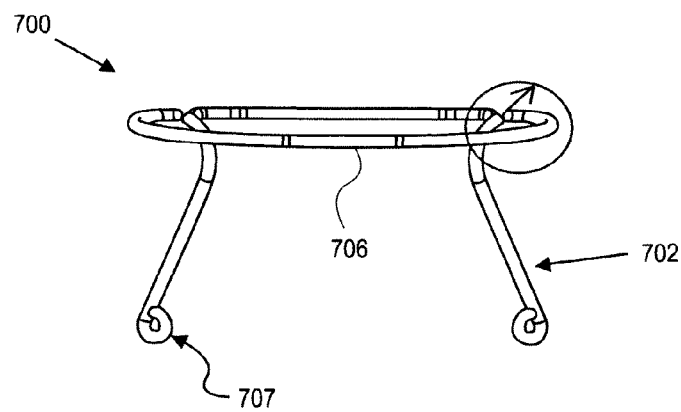
FIG. 7
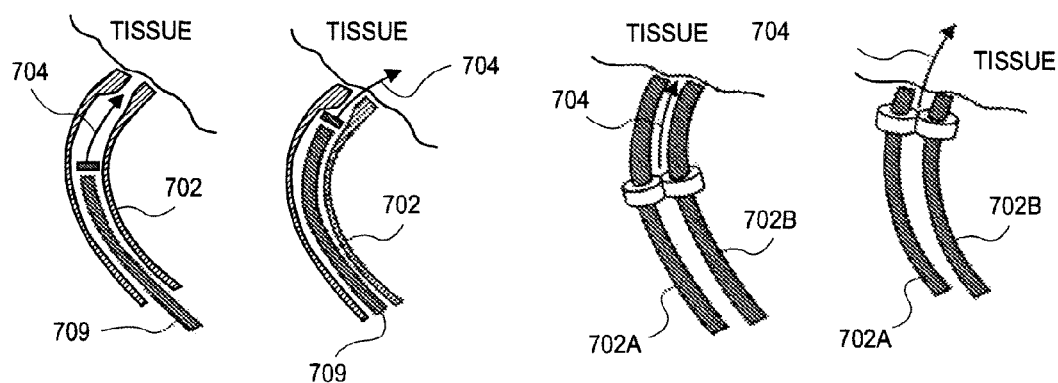
FIG. 8A   FIG. 8B   FIG. 8C   FIG. 8D

HEART VALVE PROSTHESIS WITH COLLAPSIBLE VALVE AND METHOD OF DELIVERY THEREOF

RELATED APPLICATIONS

This application is a continuation of U.S. patent application Ser. No. 12/726,338 filed on Mar. 17, 2010, which claims the benefit of priority of U.S. Provisional Patent Application Nos. 61/257,979 filed on Nov. 4, 2009, 61/227,193 filed on Jul. 21, 2009, 61/186,100 filed on Jun. 11, 2009, 61/215,944 filed on May 12, 2009, 61/212,459 filed on Apr. 13, 2009 and 61/210,255 filed on Mar. 17, 2009. The contents of the above applications are all incorporated by reference as if fully set forth herein in their entirety.

TECHNICAL FIELD

The present disclosure relates to minimally invasive surgical or percutaneous replacement and/or repair of a valve, namely the mitral valve or the tricuspid valve. More particularly, the present disclosure relates to a heart valve prosthesis with a collapsible valve and a method of delivery of the prosthesis.

BACKGROUND

The mitral valve and tricuspid valve are unidirectional heart valves that separate the atria left and right respectively, from the corresponding heart ventricles. These valves have a distinct anatomical and physiological structure, having two (mitral) or three (tricuspid) sail-like leaflets connected to a subvalvular mechanism of strings (chordae tendinae) and papillary muscles forming a part of the heart's ventricular shape, function and size.

The heart has four chambers: the right and left atria, and the right and left ventricles. The atria receive blood and then pump it into the ventricles, which then pump it out into the body.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

As noted above, these valves feature a plurality of leaflets connected to chordae tendinae and papillary muscles, which allow the leaflets to resist the high pressure developed during contractions (pumping) of the left and right ventricles.

In a healthy heart, the chords become taut, preventing the leaflets from being forced into the left or right atria and everted. Prolapse is a term used to describe the condition wherein the coaptation edges of each leaflet initially may co-apt and close, but then the leaflets rise higher and the edges separate and the valve leaks. This is normally prevented by contraction of the papillary muscles and the normal length of the chords. Contraction of the papillary muscles is simultaneous with the contraction of the ventricle and serves to keep healthy valve leaflets tightly shut at peak contraction pressures exerted by the ventricle.

Valve malfunction can result from the chords becoming stretched, and in some cases tearing. When a chord tears, the result is a flailed leaflet. Also, a normally structured valve may not function properly because of an enlargement of the valve annulus pulling the leaflets apart. This condition is referred to as a dilation of the annulus and generally results from heart muscle failure. In addition, the valve may be defective at birth or because of an acquired disease, usually infectious or inflammatory.

Diseases of the valves can cause either narrowing (stenosis) or dilatation (regurgitation, insufficiency) or a combination of those, of the valve. Surgical treatment for repair or replacement of the valves includes an open-heart procedure, extracorporeal circulation and, if replaced, a complete resection of the diseased valve.

Currently all available surgical options for valve replacement involve open heart surgery; although minimally invasive methods for valve replacement are more desirable, such methods are still in the experimental stage.

Even valves which could theoretically be provided through a non-invasive method, such as those taught by U.S. Pat. No. 7,381,220, have many drawbacks. For example, the taught valves are useful for replacement of the existing valves; however, their installation through non-invasive means is problematic. Furthermore, the valves themselves, even when installed in a manner that supports existing valve tissue, must still withstand very high pressures. Such high pressures can lead to many different types of problems, including reflux as blood returns through heart in a retrograde manner.

It may be desirable to provide a valve prosthesis that supports the mitral and/or tricuspid valve without necessarily replacing it, but instead supplements the native valve functionality by providing an adjunctive valve prosthesis, which cooperates together with the native valve for improved functionality. The background art also does not teach or suggest such a valve prosthesis which may optionally be inserted through minimally invasive surgical techniques.

SUMMARY OF INVENTION

In accordance with various aspects of the disclosure, a valve prosthesis is adapted to operate in conjunction with native heart valve leaflets. The prosthesis includes an annulus and a skirt extending from the annulus. The skirt may be configured to be positioned through a native heart valve annulus, and the skirt may be movable between an open configuration permitting blood flow through the skirt and a closed configuration blocking blood flow through the skirt in cooperation with opening and closing of the native heart valve leaflets According to various aspects, a novel valve prosthesis, for example, for a tricuspid valve and/or mitral valve, may be inserted through any one or more of a minimally invasive surgical procedure, a "traditional" operative procedure (which may for example involve open heart surgery), or a trans-catheter procedure.

The valve prosthesis, in at least some embodiments, is a (optionally non-stented) bioprosthesis attached by means of suture or any other means of bonding, to an expandable, frame (platform), which may be made from a suitable metal, including without limitation an alloy, or any type of suitable composite material (optionally including those that include metal). The frame can be made of self expanding alloy such as Nitinol (nickel/titanium alloy) or made of another metal, such as a cobalt/chrome alloy, expanded by a specialized balloon, or radial expander.

The frame engages the tissue at or near or above the top margins of the native valve (annulus). The native valve is not removed, and the ventricular shape and function are preserved. Therefore, the valve prosthesis may not replace the native valve functionality but rather supports its function.

By "native valve" or "native valve annulus" it is meant the valve or valve annulus already present in the subject, as opposed to an artificial valve or valve annulus.

According to some embodiments, the valve prosthesis comprises a support structure featuring a deployable construction adapted to be initially collapsed (crimped) in a narrow configuration suitable for introduction through a small puncture or incision into the heart cavity such as the left ventricle, the left atrium, the right atrium, the right ventricle and so forth, thereby providing access to the target location. It is further adapted to be deployed by means of removing a radial constriction such as a sheath to allow the platform to self-expand to its deployed state in the target location.

In some embodiments, the valve prosthesis optionally features a flexible film made of biological tissue such as pericardia tissue but may also optionally feature one or combination of synthetic materials, additionally or alternatively. The prosthesis may have a funnel like shape that is generally tubular and may have a variable diameter that enables flow in one direction (from the atrium to the ventricle); when the ventricle contracts, the funnel shape valve collapses and blocks any return flow from the ventricle to the atrium. Such retrograde flow is quite dangerous; over a prolonged period of time, it can lead to many deleterious health effects, including on the overall health of the heart muscle.

In an exemplary, illustrative configuration, the valve platform of the prosthesis is anchored to the ventricle wall through extensions that pass through the commissures of the native valve or at the plane of the commissures and have hooks at their ends that anchor into the ventricular wall between the chordate attachment to the ventricular wall. Furthermore, in an illustrative example, these extensions have curved ends that can be in any plane (but which may be at a 90 degree angle to the plane of both extensions) that allows a wire or cable to pass through and keep the prosthesis connected to the delivery system as long as this wire or cable is not released. The delivery action of the prosthesis may be reversible. That is, the device may optionally be refolded into the catheter after having being deployed.

In an optional embodiment, these extensions should not act on the valve in any way, including not on the valve annulus or surrounding valve tissue, nor should these extensions apply any pressure that may reshape the annulus or deform the leaflet configuration.

In an exemplary embodiment, the valve prosthesis features a "skirt" that does not restrict the motion of any of the native valve leaflets but which is situated above such leaflets, for example in the direction of the atrium (by "above" it is meant with regard to the direction of normal, not retrograde, blood flow). If the leaflets prolapse into the atrium, no blood will be able to flow into the atrium because the skirt is situated above the native valve, thus preventing retrograde blood flow into the atrium from the ventricle.

In an embodiment, the "skirt" is generally tubular in shape with a diameter that may vary and which is optionally used to complete the incompetent closure of the native valve as a whole. Thus, the skirt specifically and the valve prosthesis generally are not intended to be used as a replacement to the entire valve or in addition to only one native leaflet (in contrast to the apparatus described by Macoviak et al. in U.S. patent application publication number 2008/0065204, for example). In an exemplary embodiment, the valve skirt may be reinforced with at least one reinforcement along at least a portion of its length, for example, along the entirety of its length, in order to prevent prolapse of the skirt into the left atrium. This reinforcement is optionally an extension from the platform.

In yet another configuration, the valve "skirt" is connected to the extensions by a cable or wire in order to prevent the prolapsed of the skirt into the left atrium. These connections may optionally be an integral part of the valve platform or alternatively may be connected separately.

In an exemplary embodiment, the closing action of the native valve leaflets promotes the collapse of the prosthetic valve (skirt). Thus, during systole function, the native valve may achieve partial closure (i.e. function partially) and hence may assist the function of the valve prosthesis.

During systole, the action of the native valve leaflets is to close the passage between the left ventricle and the left atrium. In an exemplary embodiment, the leaflets, while acting as such, resist part of the pressure applied by the blood pressure in the ventricle during valve closure as well as reducing the effective area on which the pressure is applied to the valve prosthesis as a whole, thus reducing the total force applied to the prosthesis for migration into the left atrium. Depending on which valve is affected, the present invention is contemplated as a potential treatment for all forms of valvular regurgitation, such as tricuspid regurgitation, pulmonary regurgitation, mitral regurgitation, or aortic regurgitation.

BRIEF DESCRIPTION OF THE DRAWINGS

In the drawings:

FIGS. 2a-2c show an exemplary valve prosthesis according to some embodiments of the present disclosure; FIG. 2a shows the valve skirt alone, and FIGS. 2b and 2c show the valve skirt in place in the heart as an example only;

FIG. 7 shows an illustrative embodiment of an exemplary valve prosthesis in accordance with various aspects of the disclosure;

FIGS. 8A-8D show illustrative embodiments of various exemplary valve prostheses in accordance with various aspects of the disclosure;

DETAILED DESCRIPTION

The disclosure provides, in at least some embodiments, a valve prosthesis and method of insertion thereof which supports the mitral and/or tricuspid valve without replacing it. The valve prosthesis may operate to support the native valve leaflets to provide a functioning heart valve and to prevent retrograde motion of the blood, even if the native valve leaflets alone are unable to completely close and/or to prevent such retrograde motion of the blood.

Figure 1:
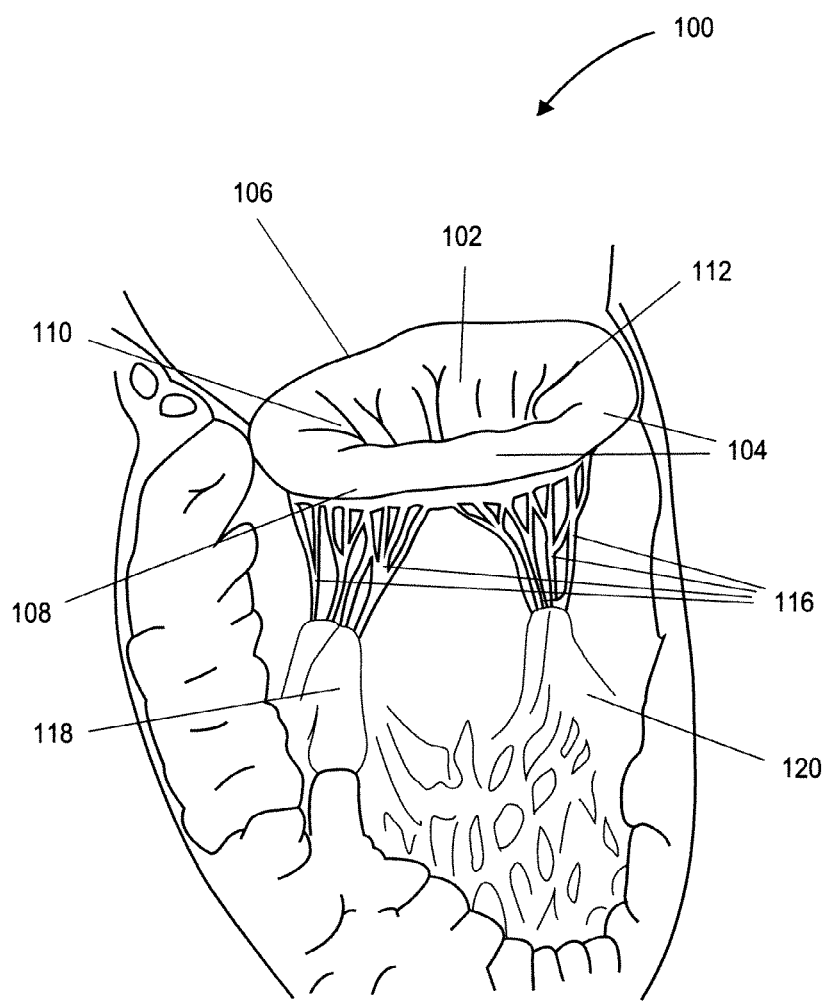
FIG. 1 shows an exemplary anatomy of a mitral valve (for reference only)

FIG. 1 shows an exemplary anatomy of a native mitral valve (for reference only). As shown, a native valve 100 features an anterior leaflet 102 and a three lobed posterior leaflet 104, which together comprise the leaflets of native valve 100, as well as an anterior annulus 106 and a posterior annulus 108, which together comprise the annulus of native valve 100. Native valve 100 also features a posterolateral commissure 110 and an anteromedial commissure 112, one or both of which are optionally used for installation of a valve prosthesis according to some embodiments of the present disclosure.

A plurality of chordinae tendinae 116 attach the leaflets to a lateral papillary muscle 118 or a medial papillary muscle 120. In a healthy heart, chordinae tendinae 116 become taut to prevent retrograde blood flow back through the leaflets. In a non-healthy heart, for a variety of reasons as described above, bloods flow in a retrograde manner through the leaflets. As described in greater detail below, in at least some embodiments of the present disclosure, the leaflets are assisted in their function by a valve prosthesis.

FIGS. 2a-2c show an exemplary valve prosthesis according to some embodiments of the present disclosure. As shown in FIG. 2a, a valve prosthesis 200 may comprise a valve skirt 202 and a prosthetic valve annulus 204 according to various aspects of the present disclosure. Although not clearly shown in FIG. 2a, in some aspects, the prosthetic valve annulus 204 may have a D-shape configuration. In some aspects, the annulus 204 may have an oval configuration.

According to various aspects, the skirt 202 may comprise a biological tissue, such as, for example, an animal (e.g., bovine or porcine tissue) or human pericardium. In some aspects, the skirt 202 may comprise a synthetic material, such as, for example, polyurethane. In various aspects, the skirt 202 may comprise a native mitral valve processed to be biologically compatible for a particular implantation. According to some aspects, the skirt 202 may comprise an ultra-thin sheet of nitinol. According to various aspects of the disclosure, the skirt 202 and/or the prothetic annulus 204 may be coated with various bioactive agents, such as anti-proliferative and/or anti-inflammatory properties or can have other properties such as antineoplastic, antiplatelet, anti-coagulant, anti-fibrin, antithrombonic, antimitotic, antibiotic, antiallergic, antioxidant as well as cystostatic agents, anti-inflammatory agents (e.g., steroidal anti-inflammatory agent, a nonsteroidal anti-inflammatory agent, or a combination thereof, and anti-proliferative agents (e.g., rapamycin and derivatives of rapamycin; everolimus and derivatives of everolimus; taxoids including taxols, docetaxel, paclitaxel, and related derivatives of taxoids, Biolimus A9, etc.). According to various aspects, the skirt may have a thickness of between about 0.05 mm and about 0.4 mm.

According to some aspects, the length of valve prosthesis 200 is at least as long as the native valve leaflets, but is not excessively long so as to avoid disturbing the flow through the aortic or adjacent valve. For example, in some aspects, the length of valve prosthesis 200 is no more than about 120% of the length of the native valve leaflets. According to various aspects, the diameter of the bottom of valve skirt 202 is at least about 80% of the diameter of the native valve area and no more than about 130% of the diameter of the native valve area.

FIG. 2b shows an exemplary valve prosthesis 200 in place in a mitral valve 100 as an illustrative example only of installation. Valve skirt 202 is shown as well, extending into a ventricle 206. FIG. 2c shows the view of FIG. 2b in cross-section. Valve skirt 202 is configured and positioned to prevent retrograde flow of blood from the ventricle 206 back into the atrium (not shown) by assisting the function of the natural, native leaflets of the mitral valve 100. It should be appreciated that the exemplary valve prosthesis 200 may also be placed in a tricuspid valve in accordance with various aspects of the disclosure.

Figure 3:
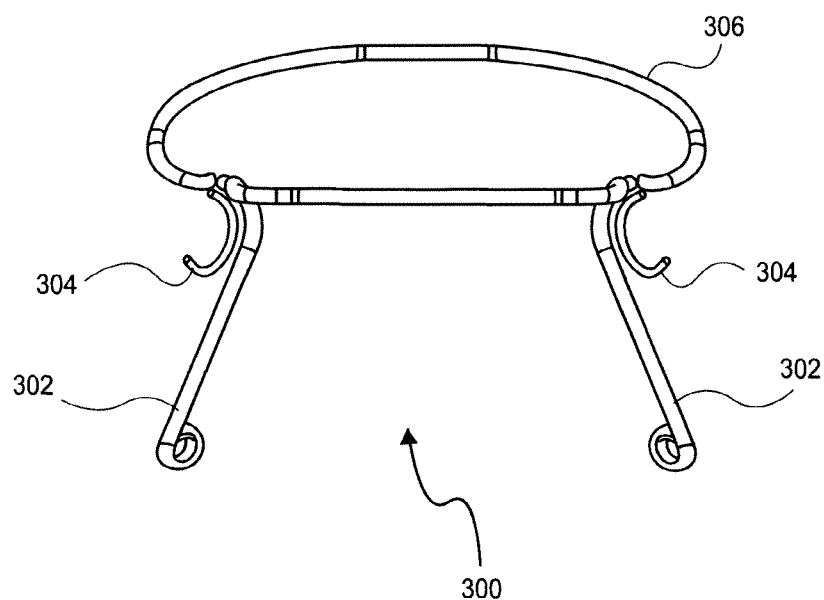
FIG. 3 shows an illustrative embodiment of an exemplary valve prosthesis in accordance with various aspects of the disclosure.

FIG. 3 shows an exemplary valve frame, or valve platform, configured to support a valve skirt of a valve prosthesis in accordance with various aspects of the present disclosure. Valve frame 300 may comprise a valve annulus 306, for example, a D-shaped annulus. According to various aspects, the semi-circular section of the D-shape may have a length at least about 1.1 to 2 times greater than that of the straight section.

According to various aspects, the valve frame 300 may comprise a wire having a diameter of about 0.3 mm to about 1.0 mm, although other diameters may be selected depending upon the material chosen for the wire, in order to maintain a desired tensile strength of the valve frame 300, as well as its ability to be folded and delivered through a catheter at least in some embodiments. Any suitable material may optionally be used for the wire as long as it retains sufficient superelasticity and may also optionally be selected from any material described herein. For example, the valve frame 300 may comprise a nickel titanium alloy (i.e., nitinol).

The valve frame 300 may include a pair of reinforcement members 302 extending from the valve annulus 306. The reinforcement members 302 are configured such that they extend along an interior surface of a valve skirt (not shown) of an exemplary valve prosthesis. The reinforcement members 302 may thus prevent the valve skirt from everting back into the atrium after deployment. The frame 300 may also include two or more hooks 304 extending from the valve annulus 306 and configured to anchor the prosthesis to the ventricle wall. In summary, the frame of valve prosthesis incorporates various anchoring members which provide stability of the valve mechanism during cardiac function, and prevent migration of the valve prosthesis over time relative to its originally deployed anatomic position. For example, the anchoring members can comprise example, hook-like members or barbs disposed at circumferentially-distributed locations along the annulus of the frame, at the distal ends of each reinforcement member. Additionally the anchoring members can also comprise expandable annulus frame designs which ensure fluid tight wall apposition along its outer periphery with the annulus of the native valve, such as by the use of a properly sized, expandable, nitinol frame, or in the alternative, the use of a radially-expandable, plastically deformable, stent-like body which cooperates with the wire frame to ensure wall apposition with the native valve annulus.

Figure 4A:
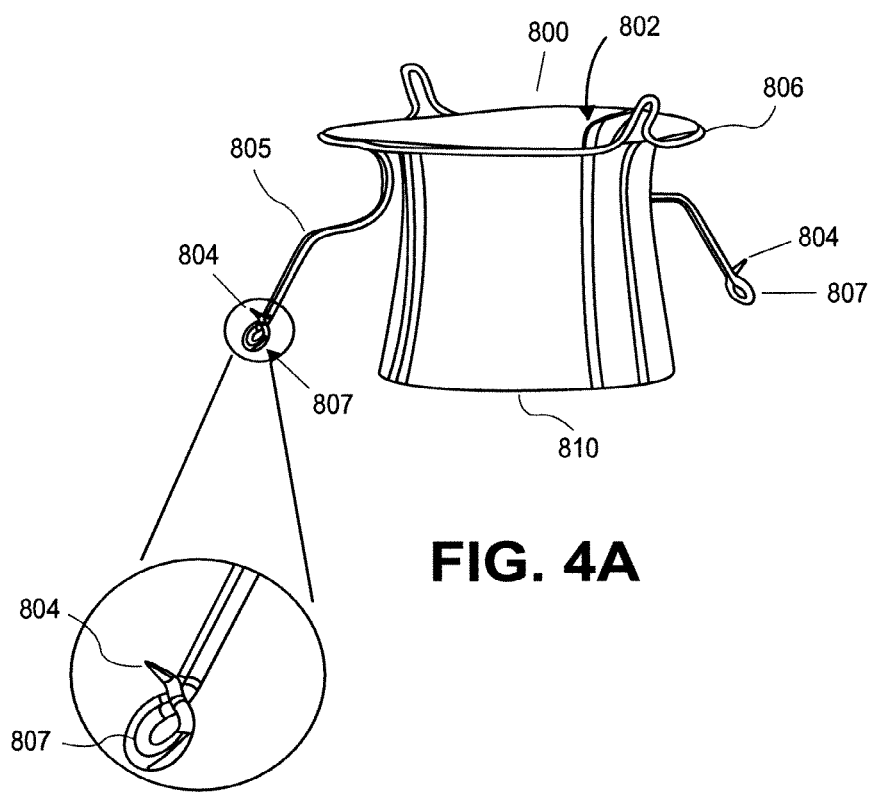
FIGS. 4a-4b show an illustrative configuration of an exemplary valve prosthesis according to some embodiments of the present disclosure.
Figure 4B:
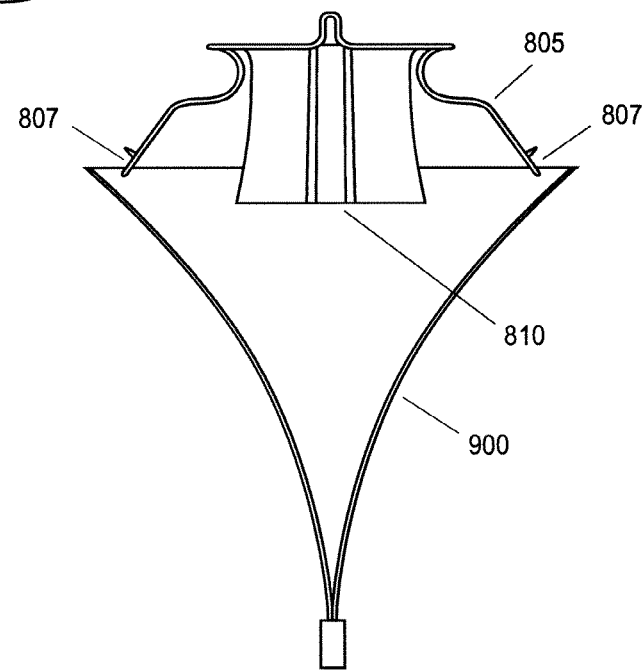

FIGS. 4a-4b show an illustrative configuration of an exemplary valve prosthesis in accordance with various aspects of the disclosure. As shown, a valve prosthesis 800 may include a valve annulus 806 with a pair of reinforcing members 802 extending therefrom through a valve skirt 810. The valve annulus 806 may include a plurality of folded loops 308. The folded loops 308 may enable the valve prosthesis 800, including the valve frame, to be folded and collapsed for delivery through a catheter, as described in greater detail below. As shown, a pair of curved, hooked extensions 805 extend from the valve annulus. The extensions 805 may include hooks 804 at its ends opposite to the valve annulus 806. The extensions may also include eyelets 807 configured to receive a delivery cable 900 (FIG. 4b) therethrough. The delivery cable 900 may pass through the eyelets 806, circle at least partially around the base of the skirt 810, and then down through the catheter (not shown), for example for adjustment of the placement of the valve prosthesis 800 at the native valve annulus, by collapsing the valve prosthesis back into the catheter for placement in a different or adjusted location. Upon installation, once the surgeon or doctor has positioned the valve prosthesis correctly, delivery cable 900 may be removed, for example, by being withdrawn through the catheter.

Figure 5:
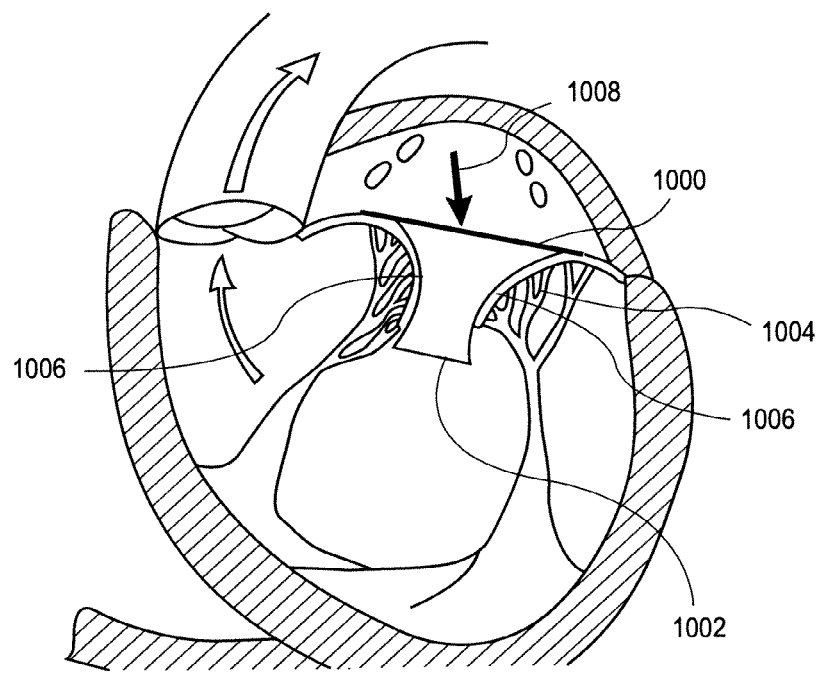
FIG. 5 shows a schematic view of the prosthetic and native mitral valve leaflets during Diastole.

FIG. 5 shows a schematic view of an exemplary prosthetic valve and the native mitral valve leaflets during diastole. As shown, a schematic valve prosthesis 1000 with a valve skirt 1002 may be installed in a native valve 1004 having a plurality of native valve leaflets 1006. The blood flow pressure gradient 1008 is also indicated by an arrow. Native valve leaflets 1006 are open, and the prosthetic valve skirt 1002 is shown as being expanded to permit blood flow.

Figure 6:
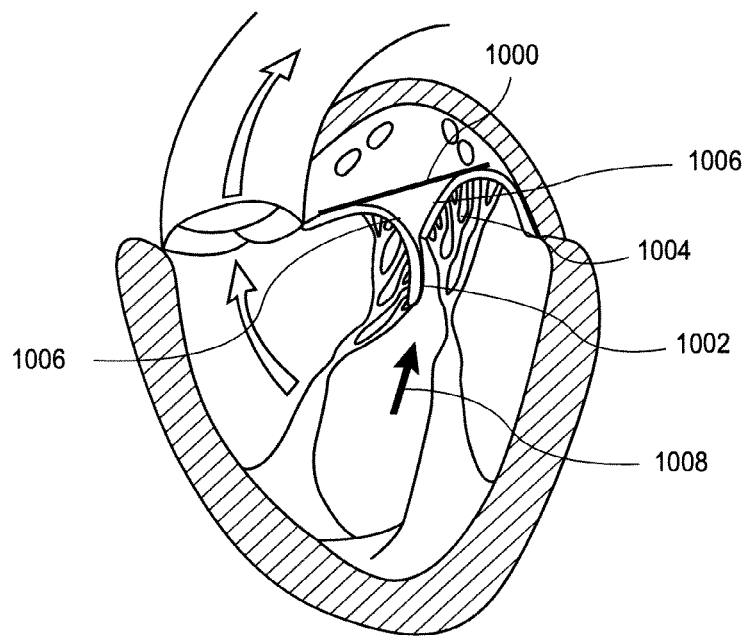
FIG. 6 shows a schematic view of the prosthetic and native mitral valve leaflets during Systole.

FIG. 6 shows a schematic view of the exemplary prosthetic valve and native mitral valve leaflets during systole, when native valve 1004 should be closed. However, native valve leaflets 1006 are only partially closed due to incomplete coaptation, resulting in valve regurgitation. Blood flow pressure gradient 1008 has now reversed, which could lead to retrograde blood flow, since valve leaflets 1006 are not completely closed. However, such retrograde blood flow is prevented by the collapse of prosthetic valve skirt 1002. The collapse of prosthetic valve skirt 1002 is assisted by the partial closure of native valve leaflets 1006.

Referring now to FIG. 7, an exemplary valve frame for a valve prosthesis in accordance with various aspects of the disclosure is described. As shown, a valve frame 700 may include a valve annulus 706 with a pair of reinforcing members 702 extending therefrom. The reinforcing members are configured to extend downwardly through the interior of a valve skirt (not shown) to prevent eversion of the valve skirt after deployment to a heart valve. The reinforcing members 702 may include eyelets 707 at, for example, the ends of the reinforcing members 702 opposite the valve annulus 706. It should be appreciated that the valve annulus 706 may include a plurality of folded loops (not shown) to enable the valve prosthesis, including the valve frame 700, to be folded and collapsed for delivery through a catheter, as described in greater detail below.

The valve frame 700 may include a pair of hooks 704 (only one shown in FIG. 7) for anchoring the prosthesis in position relative to the native heart valve. The hooks 704 may be slidable relative to the reinforcing members 702 between an unexposed, delivery position and an exposed, anchoring position.

For example, as shown in FIGS. 8a and 8b, each hook 704 may be slidable within a hollow reinforcing member 702. The hollow reinforcing member 702 has an opening sized and configured to permit passage of an anchoring portion of the hook 704 curved, while retaining a base portion of the hook 704 that has a larger diameter than the hollow lumen of the reinforcing member. The hook 704 may be pushed out of the reinforcing member 702 by a pusher 709 that is an element of a delivery system which is operable by a user.

Figure 9:
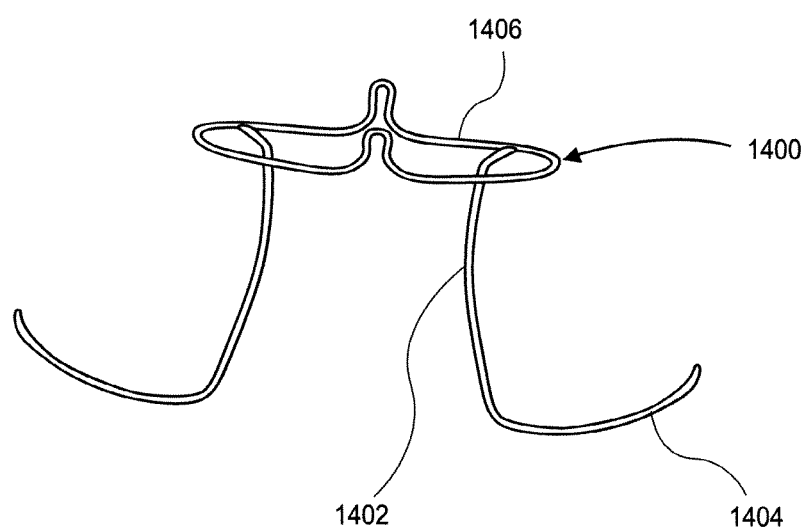
FIG. 9 shows an exemplary frame for a valve prosthesis in accordance with various aspects of the disclosure.

As shown in FIGS. 8c and 8d, each reinforcing member 702 may comprise two reinforcing elements 702a, 702b. The hook 704 is coupled to a sliding member 711 coupled to both reinforcing elements 702a, 702b. As shown, the hook 704 may be slidable relative to the reinforcing members 702 between an unexposed, delivery position and an exposed, anchoring position. For example, as shown in FIGS. 8c and 8d, each hook 704 may be slidable between a pair of reinforcing members 702a, 702b. The reinforcing members 702a, 702b may include a stop member (not shown) for preventing the hook from being slid off the reinforcing members 702a, 702b. The hook 704 may be pushed to the exposed, anchoring position by a pusher (not shown) that is an element of a delivery system which is operable by a user Referring now to FIG. 9, an exemplary valve frame for a valve prosthesis in accordance with various aspects of the disclosure is described. As shown, a valve frame 1400 may include a valve annulus 1406 with a pair of reinforcing members 1402 extending therefrom. The reinforcing members 1402 may be configured to extend downwardly through the interior of a valve skirt (not shown) to prevent eversion of the valve skirt after deployment to a heart valve. The reinforcing members 1402 may be configured such that the ends of the reinforcing members 1402 distal to the valve annulus 1406 comprise hooks 1404 for anchoring the valve prosthesis, including the valve frame 1400, in position relative to the native heart valve.

Figure 10:
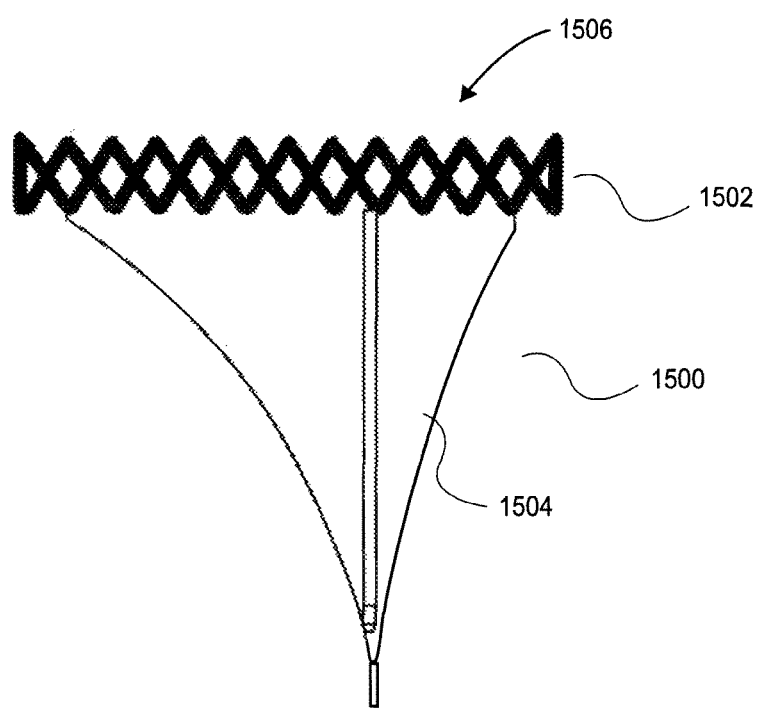
FIG. 10 shows an exemplary valve prosthesis in accordance with various aspects of the disclosure.

FIG. 10 shows an illustrative configuration of an exemplary valve prosthesis in accordance with various aspects of the disclosure. As shown, a valve prosthesis 1500 may include a valve frame annulus 1506 comprising an expandable stent 1502. According to various aspects, the stent may be self expanding or balloon inflated (e.g., plastically expandable), for example, to hold the valve prosthesis 1500 in position relative to the native heart valve. A valve skirt 1504 may extend from the expandable stent 1502.

Figure 11:
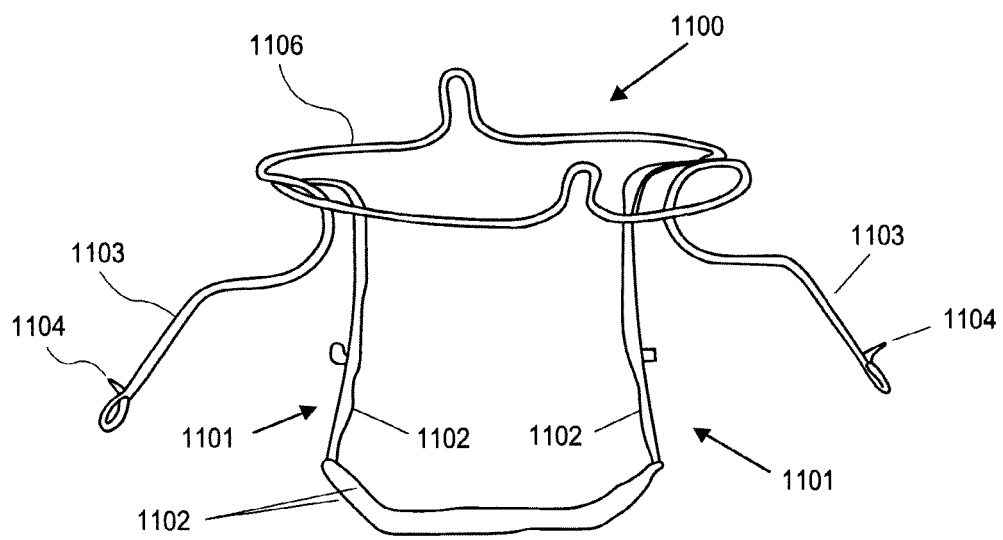
FIG. 11 shows an exemplary frame for a valve prosthesis in accordance with various aspects of the disclosure.

Referring now to FIG. 11, an exemplary valve frame, or valve platform, configured to support a valve skirt of a valve prosthesis in accordance with various aspects of the present disclosure is described. Valve frame 1100 may comprise a valve annulus 1106, for example, a D-shaped or oval annulus. According to various aspects, the valve frame 1100 may comprise a wire having a diameter of about 0.3 mm to about 1.0 mm, although other diameters may be selected depending upon the material chosen for the wire, in order to maintain a desired tensile strength of the valve frame 1100, as well as its ability to be folded and delivered through a catheter at least in some embodiments. Any suitable material may optionally be used for the wire as long as it retains sufficient superelasticity and may also optionally be selected from any material described herein. For example, the valve frame 1100 may comprise a nickel titanium alloy (i.e., nitinol).

The valve frame 1100 may include a pair of reinforcement members 1101 extending from the valve annulus 1106. The reinforcement members 1101 comprise a wire loop 1102 that extends from the valve annulus 1106 along an interior surface of a valve skirt (not shown) to a distal end of the valve skirt opposite the annulus 1106 along the distal edge of the valve shirt and back to the valve annulus 1106 along an interior surface of the valve skirt. The wire loop 1102 then extends away from the valve annulus 1106 along an interior surface of the valve skirt in a direction toward the distal end of the valve skirt, along the distal edge of the valve skirt, and back to the valve annulus 1106 along an interior surface of the valve skirt to complete the loop. The reinforcement members 1101 may thus prevent the valve skirt from everting back into the atrium after deployment.

According to various aspects, the reinforcement members of the disclosure may be secured, for example, by suturing, to the valve skirt at any or all locations coextensive between the reinforcement member and the valve skirt.

As shown, a pair of curved, hooked extensions 1103 extend from the valve annulus 1106. The extensions 1103 may include hooks 1104 at their ends opposite to the valve annulus 1106. The extensions 1103 may also include eyelets (unnumbered) configured to receive a delivery cable (not shown) therethrough. Alternatively or additionally, the reinforcement members 1101 may include eyelets configured to receive a delivery cable.

Figure 12A:
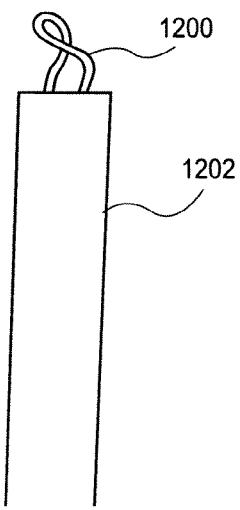
FIGS. 12A-12D show an exemplary prosthesis in its folded state and as it unfolds from a catheter.

FIGS. 12a-12d show the prosthesis in its folded state and as it unfolds from a catheter. As shown in FIG. 12a, a valve prosthesis 1200 (shown as the frame only for the purpose of description and without any intention of being limiting) is shown completely folded into a catheter 1202 (it is possible that valve prosthesis 1200 could be so completely collapsed that no portion is visible; however, for a clearer illustration, a part of valve prosthesis 1200 is shown slightly protruding from catheter 1202).

Figure 12B:
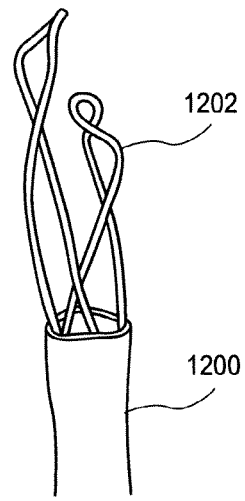
Figure 12C:
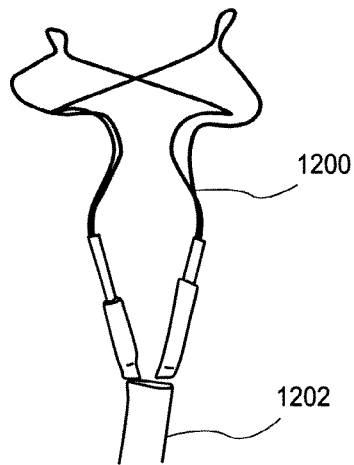

In FIG. 12b, valve prosthesis 1200 starts to emerge from catheter 1202; in FIG. 12c, valve prosthesis 1200 continues to emerge from catheter 1202.

Figure 12D:
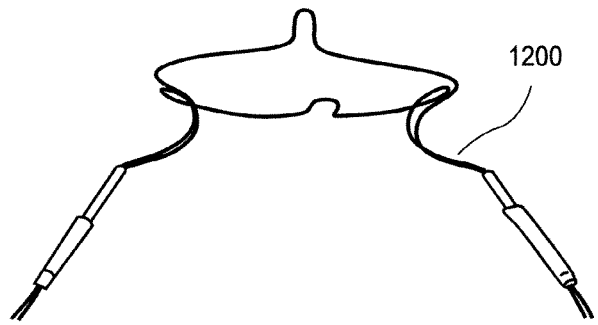

FIG. 12d shows valve prosthesis 1200 completely emerged from catheter 1202 and ready for installation on the native valve annulus Referring now to FIGS. 13a-13d, an illustrative configuration of an exemplary valve prosthesis in accordance with various aspects of the disclosure is depicted. As shown, a valve prosthesis 1300 may include a valve annulus 1306 such as, for example, a D-shaped annulus. The valve annulus 1306 may include a plurality of folded loops 1308. The folded loops 308 may enable the valve prosthesis 800, including the valve frame, to be folded and collapsed for delivery through a catheter.

Figure 13B:
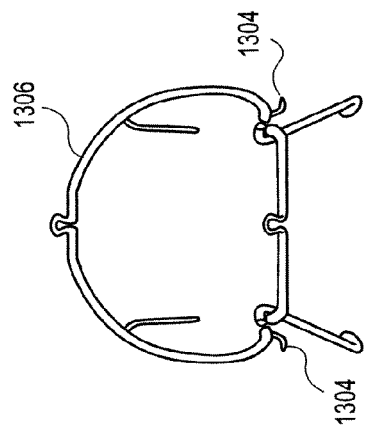
FIGS. 13A-13D show an exemplary valve prosthesis in accordance with various aspects of the disclosure.
Figure 13D:
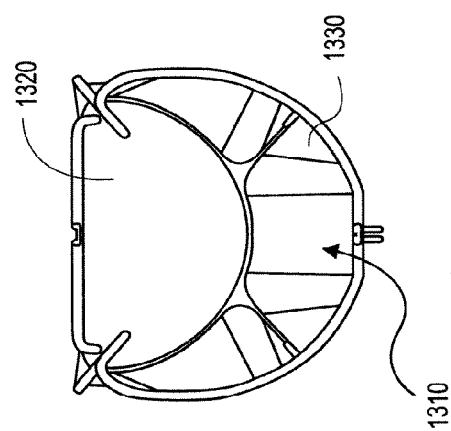
Figure 13A:
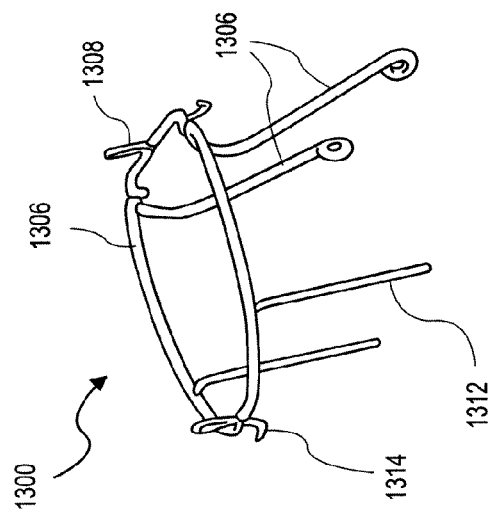
Figure 13C:
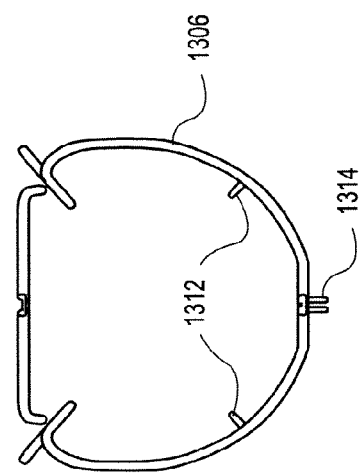

A first pair of reinforcing members 1302 may extend from the annulus 1306 through an interior of a valve skirt 1310 (FIG. 13d). According to some aspects, the reinforcing members 1302 may extend from each end of the substantially straight portion of the D-shaped annulus 1306. The extensions may also include eyelets 1307 configured to receive a delivery cable (not shown) therethrough. In some aspects, a pair of hooks 1304 extend from the valve annulus 106 proximate the reinforcing members 1302. According to various aspects, a third hook 1314 may be provided at a region of the curved portion of the D-shaped annulus 1306 that is furthest from the straight portion of the annulus 1306 or at the approximate midpoint of the curved portion. The hooks 1304, 1314 may be configured to anchor the valve prosthesis 1300 in position at the native heart valve. The extensions 805 may include hooks 804 at its ends opposite to the valve annulus 806.

A second pair of reinforcing members 1322 may extend from the valve annulus 1306 along the inner surface of the valve skirt 1310 (FIG. 13d). According to some aspects, the second pair of reinforcing members 1322 may extend from regions of the curved portion of the D-shaped annulus 1306 in opposition to the first pair of reinforcing members 1312.

Referring now to FIG. 13d, the valve skirt 1310 may comprise a first skirt portion 1320 and a second skirt portion 1330. When the valve skirt 1310 is urged to a closed position coaptation by the normal pressure gradient between the ventricle and atrium, the second pair of reinforcing members 1322 cause the second skirt member 1330 to close around the second pair of reinforcing members 1322, thus giving the appearance from a top view of the valve prosthesis (FIG. 13d) that the valve skirt 1310 has four leaflets instead of two valve skirt portions.

Figure 14A:
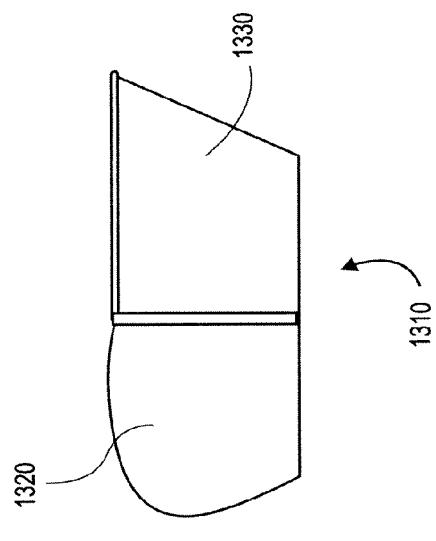
FIGS. 14A to 14D show an exemplary skirt for a valve prosthesis in accordance with various aspects of the disclosure.
Figure 14B:
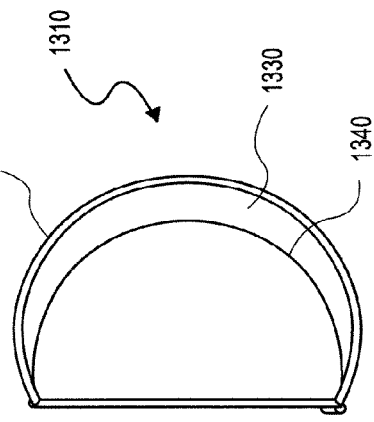
Figure 14C:
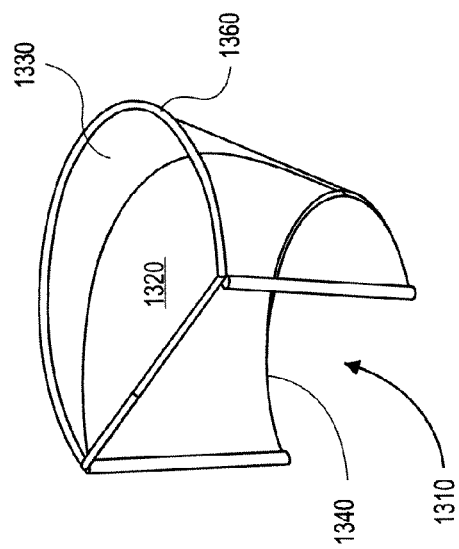
Figure 14D:
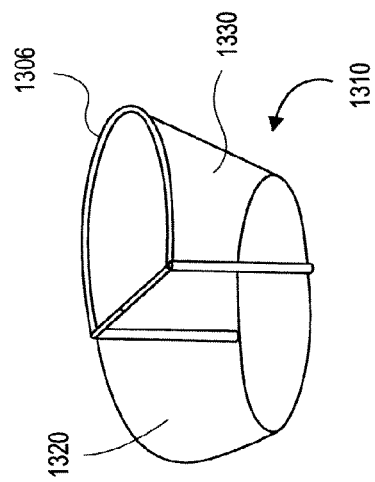

FIGS. 14a-14d illustrate an exemplary valve skirt 1310 of a valve prosthesis in accordance with various aspects of the disclosure. FIGS. 14a and 14d illustrate the valve skirt 1310 in a relaxed yet substantially closed configuration, while FIGS. 14b and 14c illustrate the valve skirt 1310 in an expanded ex vivo configuration. As shown, the valve skirt 1310 includes a first skirt portion 1320 and a second skirt portion 1330. As shown in FIGS. 14a and 14d, the region 1340 of the valve skirt 1310 where the first and second skirt portions 1320, 1330 meet in a relaxed yet substantially closed configuration along a curved segment to form a D-shape similar to that of the valve annulus 1306. Further, the D-shaped annulus 1306 and D-shaped closure region 1340 are similar to those of the native heart valve.

Figure 15:
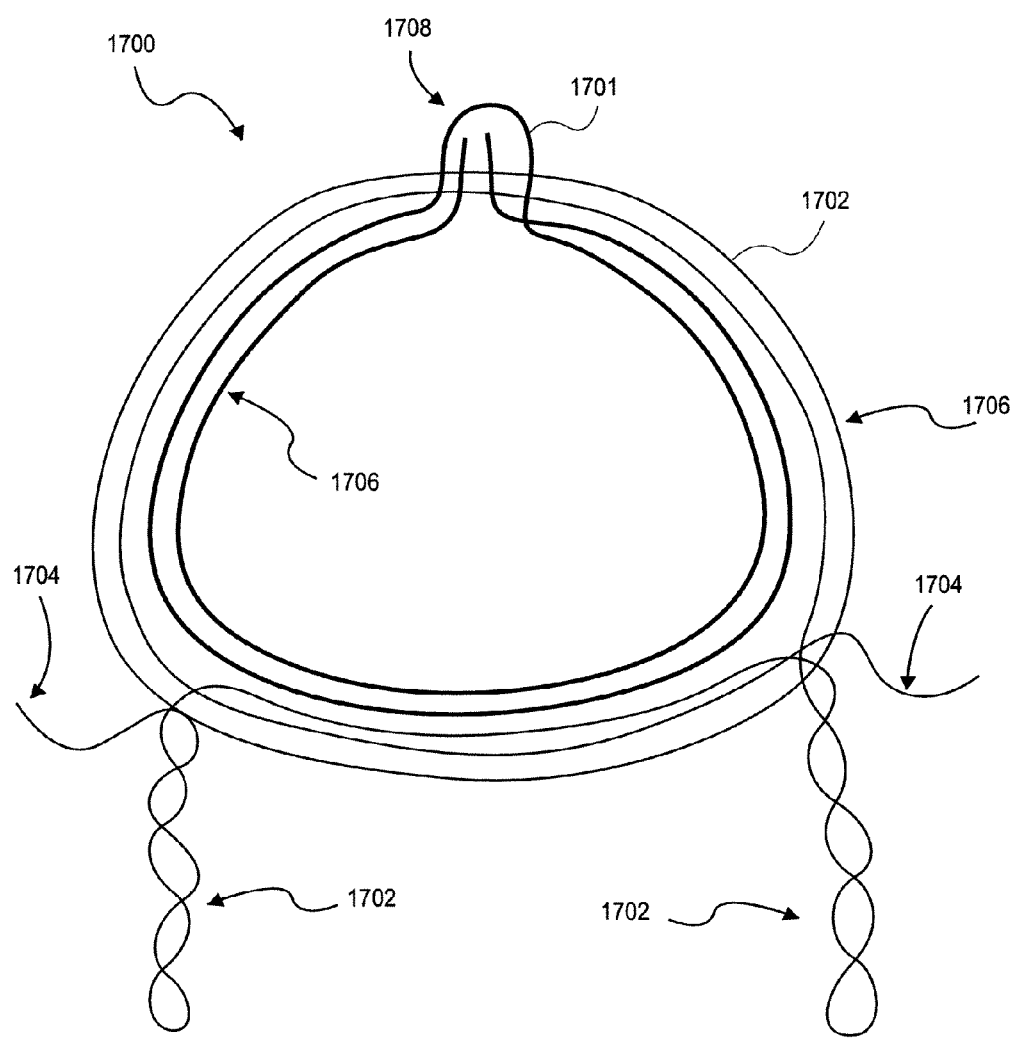
FIG. 15 shows an exemplary delivery system for a valve prosthesis in accordance with various aspects of the disclosure.

Referring now to FIG. 15, an exemplary valve prosthesis in accordance with various aspects of the disclosure is described. As shown, the exemplary prosthesis 1700 can be configured from two wires 1701, 1702 twisted and wound together. As illustrated, the first wire 1701 may define a portion of the valve annulus 1706 and at least one folded loop 1708 as well as one or more hooks (1314) at the apex of the curved part of the D-shape. The second wire 1702 may define a further portion of the valve annulus 1706, one or more hooks 1704, and one or more reinforcing members 1702.

Figure 16:
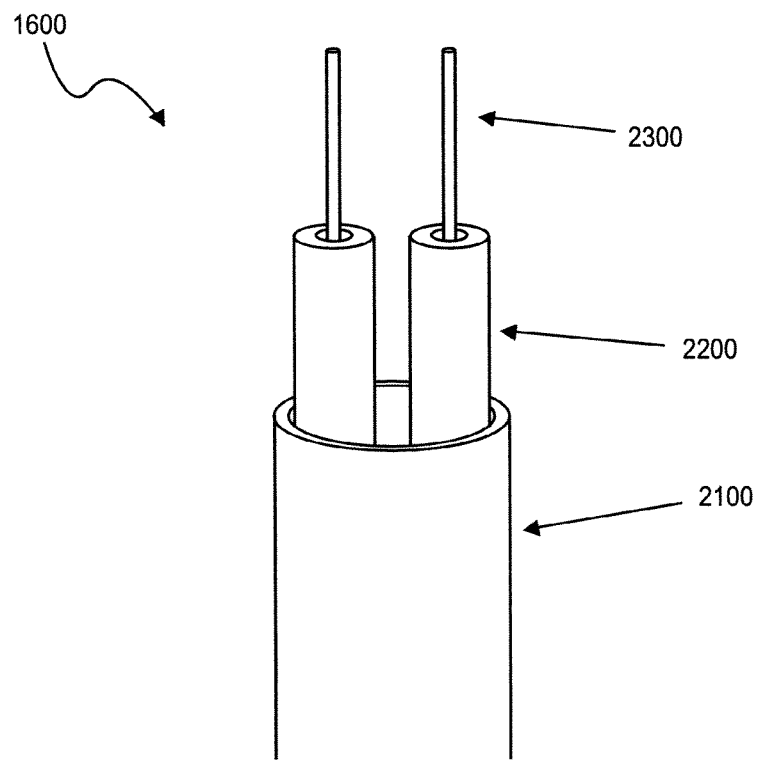
FIG. 16 shows a portion of an exemplary delivery system valve prosthesis in accordance with various aspects of the disclosure.
Figure 17:
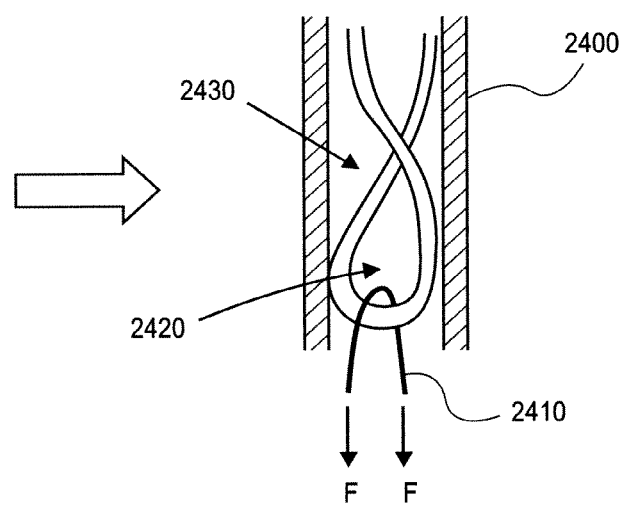
FIG. 17 shows a portion of an exemplary delivery system valve prosthesis in accordance with various aspects of the disclosure.

FIGS. 16 and 17 show portion of an exemplary delivery system for delivering and deploying a valve prosthesis in accordance with various aspects of the disclosure. FIG. 16 illustrates a delivery system 1600 including an outer sheath 2100, two inner sheaths 2200, and two cables or rods 2300. The inner sheaths 2200 may be disposed in the outer sheath 2100 and may be exposed, for example, by pulling the outer sheath 2100 in a proximal direction relative to the inner sheaths 2200. Similarly, one cable or rod 2300 may be disposed in each of the inner sheaths 2200. The cable or rod 2300 may be exposed, for example, by pulling the inner sheath 2200 in a proximal direction relative to the cable or rod 2300. According to various aspects, the cable or rods 2300 may be coupled to one or more reinforcing members, hooks, and/or extensions of a valve prosthesis, for example, by passing through eyelets provided on the one or more reinforcing members, hooks, and/or extensions of the valve prosthesis. The cables or rods 2300 can operate as pushers for moving hooks from a withdrawn position to an anchoring position in accordance with various aspects of the disclosure.

Referring now to FIG. 17, any of the aforementioned hooks used for anchoring the valve prosthesis to tissue can be folded for delivery into a tubular sheath 2400. The various hooks can be pulled into the sheath 2400 by passing a wire or cable 2410 through an eyelet 2420 of the hook 2430 and pulling the hook 2430 into the sheath 2400 with the wire or cable 2410. The sheath 2400 can be retracted to deploy the hook 2430 upon delivery.

Figure 18:
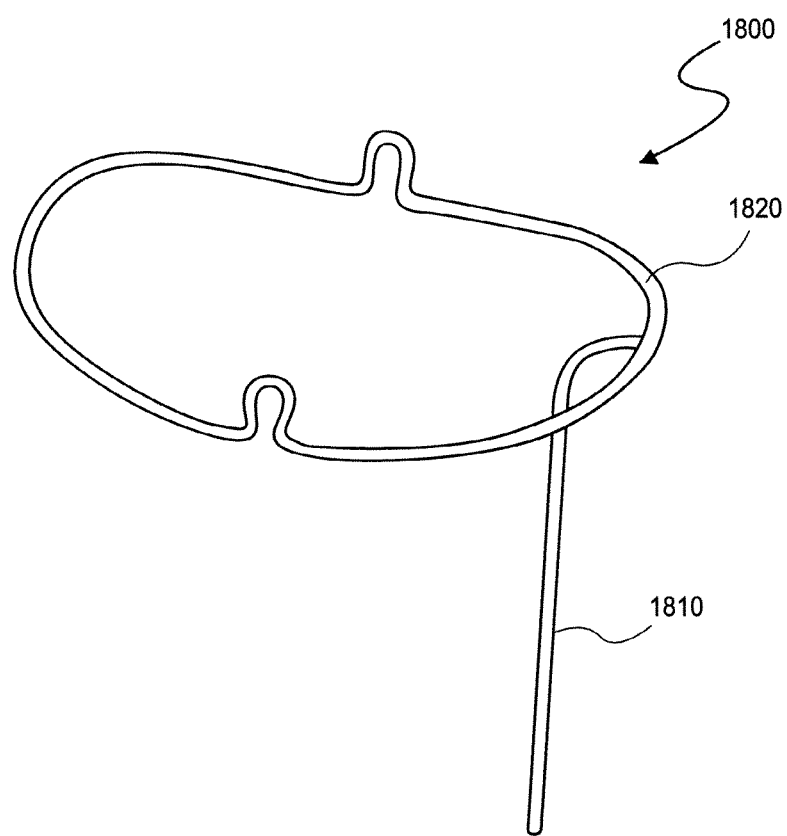
FIG. 18 is an exemplary measuring device for use in delivery of a valve prosthesis in accordance with various aspects of the disclosure.

FIG. 18 illustrates an exemplary tool, for example, measuring frame 1800, for use with an exemplary method for delivering a valve prosthesis in accordance with various aspects of the disclosure. The measuring frame 1800 includes a single leg 1810 extending from an annulus 1820. The annulus 1820 may include markings (not shown) to help size the native valve annulus as described below. Use of the tool is described in connection with the method illustrated in FIG. 19 below.

Figure 19:
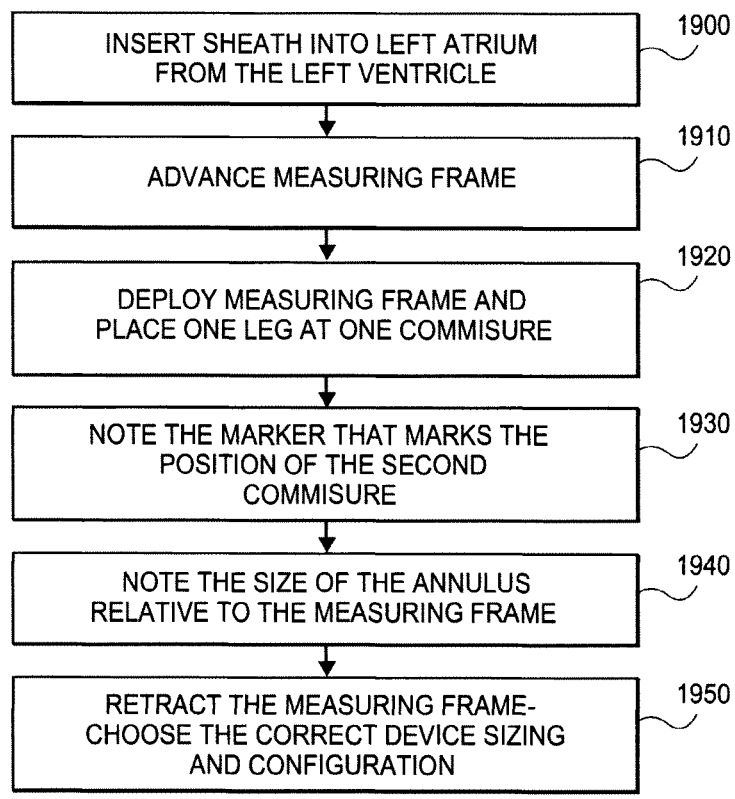
FIG. 19 is a flow chart of an exemplary delivery method of a valve prosthesis in accordance with various aspects of the disclosure.

Referring now to FIG. 19, an exemplary pre-delivery procedure is described with respect to the provided flow chart. The pre-delivery process begins at step 1900 where a sheath containing the measuring frame 1800 is inserted into the left atrium from the left ventricle. The process continues to step 1910 where the measuring frame 1800 is advanced from the sheath. Then, in step 1920, the measuring frame 1800 is deployed such that the leg 1810 is at one commissure of a heart valve. The process proceeds to step 1930.

In step 1930, the user observes which one of various markers, for example, radiopaque markers, on the annulus 1820 aligns with the second commissure of the heart valve. Next, in step 1940, the user notes the size of the annulus relative to the measuring frame 1800. The process concludes in step 1950 where the measuring frame 1800 is retracted into the sheath and the correct size and configuration for a valve prosthesis is selected.

Figure 20:
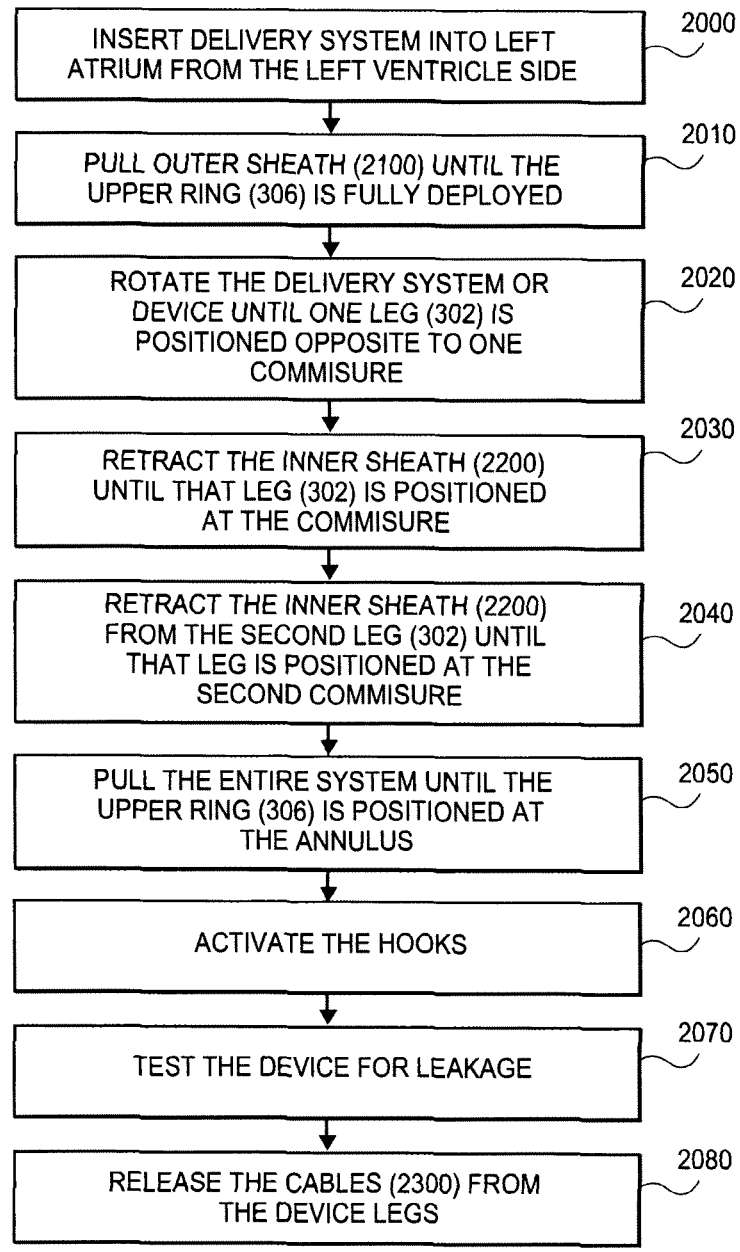
FIG. 20 is a flow chart of an exemplary pre-delivery method of a valve prosthesis in accordance with various aspects of the disclosure.

FIG. 20 is a flow chart showing an exemplary method for delivering a valve prosthesis in accordance with various aspects of the disclosure. The method begins at step 2000 where a delivery system is inserted into the left atrium from the left ventricle. The process proceeds to step 2010 where the outer sheath 2100 is pulled proximally until a valve annulus is fully deployed. The process then goes to step 2020.

In step 2020, the delivery system is rotated until a first leg of the valve prosthesis is positioned opposite to one commissure of the heart valve. The process continues to step 2030 where the inner sheath 2200 associated with the first leg is retracted until the first leg is positioned at the commissure. The process then proceeds to step 2040 where the inner sheath 2200 associated with the second leg is retracted until the second leg is positioned at the second commissure. The process continues to step 2050.

Next in step 2050, the entire delivery system 1600 is retracted proximally until the valve annulus is positioned at the native valve annulus. Then, in step 2060, the hooks are activated either by being pushed into an anchoring position or by retraction of a tubular sheath enclosed the hooks. The process continues to step 2070 where the device is tested for leakage by observing the flow across the valve using such means as ultrasound. For example, various pre-treatment and post-treatment diagnostic techniques are available for assessing valvular sufficiency and/or leakage, such as transthoracic, echo-Doppler based echocardiography (TTE), and transesophageal, echo-Doppler based echocardiography (TEE); cardiac catherization with radiopaque dye; stress tests; and other known techniques. The process then concludes at step 2080 where the cables 2300 are withdrawn to release the reinforcing members.

It would be appreciated by persons skilled in the art that radiopaque markers can be incorporated into the valve prosthesis such as by the use of radiopaque material, for example, tantalum, platinum, and/or gold, which may be physically secured to the valve frame such as by collars crimped or welded on the frame at various locations along the annulus and/or the skirt and/or at the distal ends of the reinforcement members. Alternatively, radiopaque markers can be practice by use of gold thread woven into desired locations of the valve skirt.

It will be apparent to those skilled in the art that various modifications and variations can be made to the heart valve prosthesis and method of delivery of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A prosthetic cardiac valve support device comprising:
   an annular support element configured for positioning at or near a native heart valve annulus;
   at least two valve support extensions shaped to extend through commissures of the native heart valve for supporting a flexible valve; and
   at least two anchoring extensions:
   attached at one end to said annular support element, and extending in an opposite direction towards an unattached end;
   in a form of hooks shaped for anchoring said annular support element to tissue;
   all of the anchoring extensions being adapted to extend through commissures of a native heart valve without interfering with movement of native heart valve leaflets; and
   the anchoring extensions shaped to prevent said annular support element from shifting upstream relative to the native heart valve annulus.

2. The device of claim 1 in which said anchoring extensions are shaped to extend below an annulus of the native heart valve.

3. The device of claim 1 in which said anchoring extensions are attached to approximately opposing edges of the annular support element.

4. The device of claim 1 in which said anchoring extensions are attached to said annular support element at non-opposing positions around said annular support element, conforming to positions of commissures of the native heart valve.

5. The device of claim 1 in which all of said anchoring extensions are shaped to extend through commissures of a native heart valve and extend radially outward from a valve center, further than native heart valve leaflets, without interfering with closing of native heart valve leaflets.

6. The device of claim 1 in which said valve support extensions are connected to each other at tips of the valve support extensions distal from an attachment of said support extensions to said annular support element.

7. The device of claim 1 in which said anchoring extensions comprises a loop at a tip of said anchoring extensions.

8. The device of claim 1, wherein a part of said annular support element is a D-shaped annulus element conforming to a shape of a mitral valve annulus.

9. The device of claim 1, wherein said annular support element is elastically deformable.

10. The device of claim 1, in which said unattached end of said anchoring extensions are shaped to extend through the native heart valve annulus and are curved in a direction from a center of the native heart valve annulus toward heart walls.

11. A method for providing support for a cardiac valve comprising:
    placing an annular support element for a cardiac valve upstream of a native heart valve annulus;
    extending at least two valve support extensions shaped to extend through commissures of the native heart valve for supporting a flexible valve;
    extending at least two anchoring extensions:
    attached at one end to said annular support element and extending in an opposite direction towards an unattached end;
    in a form of hooks shaped for anchoring said annular support element to tissue; and
    all of the anchoring extensions being adapted to extend through commissures of a native heart valve without interfering with movement of native heart valve leaflets,
    so as to prevent said annular support element from shifting upstream relative to the native heart valve annulus.

12. The method of claim 11 in which the anchoring extensions are anchored in tissue.

13. The method of claim 11 in which the anchoring extensions extend below an annulus of the native heart valve.

14. The method of claim 11 in which said anchoring extensions are extended through commissures of a native heart valve without interfering with movement of native heart valve leaflets.

15. The method of claim 11 in which all of said anchoring extensions are extended through commissures of a native heart valve and extended radially outward from a valve center, further than native heart valve leaflets without interfering with closing of native heart valve leaflets.

16. The method of claim 11 in which the cardiac valve comprises a flexible valve, and further comprising extending at least two valve support extensions for supporting said flexible valve through commissures of the native heart valve.

17. The method of claim 11 in which said placing said annular support element upstream of a native heart valve annulus comprises expanding said annular support element radially like a stent.

* * * * *